(12) United States Patent
Blatter et al.

(10) Patent No.: US 6,503,948 B2
(45) Date of Patent: Jan. 7, 2003

(54) METHOD FOR PREVENTION OR TREATMENT OF ACUTE ALLOGRAFT REJECTION AND A PHARMACEUTICAL COMPOSITION THEREFOR

(75) Inventors: Herbert M. Blatter, Birmingham, AL (US); Donald R. Kahn, Mountain Brook, AL (US); James R. Piper, Birmingham, AL (US); John A. Secrist, III, Birmingham, AL (US); Robert F. Struck, Birmingham, AL (US); Carroll Temple, Seaside, FL (US)

(73) Assignee: Southern Research Institute, Birmingham, AL (US)

( * ) Notice: Subject to any disclaimer, the term of this patent is extended or adjusted under 35 U.S.C. 154(b) by 0 days.

(21) Appl. No.: 10/123,185

(22) Filed: Apr. 17, 2002

(65) Prior Publication Data

US 2002/0151601 A1 Oct. 17, 2002

Related U.S. Application Data

(63) Continuation of application No. 09/221,602, filed on Dec. 29, 1998, now abandoned.

(51) Int. Cl.$^7$ .............................................. A61K 31/175

(52) U.S. Cl. ........................... 514/589; 514/23; 514/42; 514/348; 514/352; 514/353; 514/354; 514/885; 514/9

(58) Field of Search ........................... 514/589, 23, 42, 514/348, 352, 353, 354, 885, 9

(56) References Cited

U.S. PATENT DOCUMENTS 4,377,687 A * 3/1983 Eisenbrand ................. 544/164

OTHER PUBLICATIONS

Soots et al, "Prolongation of Rat Cardiac Allograft Survival by Donor Pretreatment", Transplantation, vol. 25, No. 5, pp. 259–264 (1978).*

* cited by examiner

Primary Examiner—Frederick Krass
(74) Attorney, Agent, or Firm—Connolly Bove Lodge & Hutz LLP

(57) ABSTRACT

A method for treating an organ donor prior to harvesting organ to reduce graft rejection in a recipient. An amount effective to reduce graft rejection of at least one compound selected from the group consisting of compounds having formulas I, II, III, IV, V, VI, and VII is administered to the organ donor:

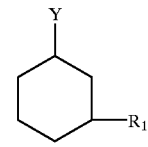

I

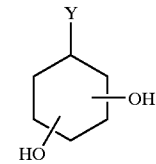

II

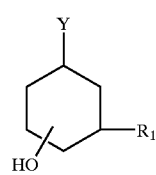

III

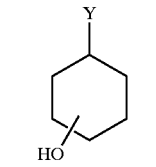

IV

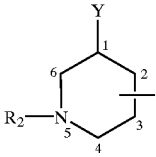

V

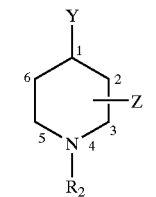

VI

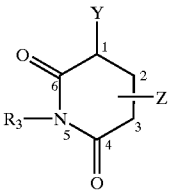

VII wherein
Y is

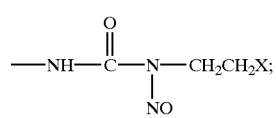

X is F or Cl; and the remaining groups are as defined in the specification.

14 Claims, No Drawings

METHOD FOR PREVENTION OR TREATMENT OF ACUTE ALLOGRAFT REJECTION AND A PHARMACEUTICAL COMPOSITION THEREFOR

This application is a continuation of U.S. Ser. No. 09/221,602, filed Dec. 29, 1998, and now abandoned.

FIELD OF THE INVENTION

The invention relates to the field of organ transplantation. In particular, the present invention relates to methods for helping to prevent rejection of organ transplants by the recipient. The present invention also relates to pharmaceutical compositions for helping to prevent rejection of organ transplants by treatment of the donor.

BACKGROUND OF THE INVENTION

Throughout the brief history of organ transplant surgery, included in the broader term "allograft", research has rapidly progressed to the point where many transplant surgeries are now considered routine procedures. In fact, we have moved from the time of the first successful organ transplant in just the latter half of this century to the point where, for example kidney transplants, are considered somewhat routine. However, in spite of the frequency with which organ transplants are now carried out, great hurdles remain to be overcome.

After transplant surgery, the greatest challenge for physicians is to prevent graft rejection by the recipient's immune system and to prevent infections caused by the immunosuppressant treatment of the recipient. Immune response of an organ transplant recipient includes activation of the recipient's T-cells. Immune systems of animals are designed such that they help to protect the body by attacking anything in the body that the body does not recognize. In this way, immune systems help to combat foreign bodies, such as viruses and bacteria that find their way into a body.

In the same manner that a virus or bacteria represents a foreign substance to a body's immune system, an organ from a donor represents foreign matter to the immune system of the recipient. No matter how well the characteristics of the recipient and the donor match, such as blood groups and other histocompatibility factors, organ transplant will still act as a foreign substance for the purposes of inducing an immune response in a recipient's body. As stated above, the immune response to an organ transplant, typically referred to as an allograft, includes the activation of T-cells.

As a result, after transplantation, it is necessary that the immune system of the recipient be controlled as much as possible to prevent graft rejection. Currently, the success of organ transplant surgery is highly dependent on an immunosuppression regimen initiated at the time or before transplantation. Such immune suppressing activity must continue for the remainder of the patient's life. Typically, conventual immunosuppression therapy includes at least one immunosuppressing drug administered to the recipient. These drugs include Cyclosporine, Azathioprine, steroids, Tacrolimus, and/or Mycophenolate Mofetil. Any one or more of these drugs may be administered individually or in combination, simultaneously or successively to suppress immune response in the recipient's body. These drugs act non specifically and broadly impair the recipient's immune system to reduce the immune response against the graft.

Typically, even with the use of immunosuppressants, patients have a risk of about 5% to about 20% per year of losing grafts during the first three years following transplantation. Furthermore, less than 50% of patients receiving organs from unrelated donors have functioning grafts after 10 years. Along these lines, there have been well publicized cases of patients requiring multiple transplant surgeries as their bodies reject graft after graft.

Not only do patients risk rejection of organ transplants, but inherent in the term "immunosuppressing" drugs is the fact that the drugs suppress the immune systems of the patients. As a result, transplant patients are more susceptible to contracting infections. This may be particularly damaging to transplant patients in the time just after receiving the transplanted organ since the patients will also be weak as a result of undergoing major surgery. Additionally, at this time, it is desired for transplant patients to heal. In other words, it is desired that the transplant recipient's body expend energy in healing and incorporating the transplanted organ into the body rather than fighting to reject the organ or fighting infections resulting from a compromised immune system. Moreover, one should keep in mind that infection is a major cause of death at anytime after transplant because the recipient must always take immunosuppressive drugs.

SUMMARY OF THE INVENTION

The present invention provides a method for addressing the above-described as well as other problems by providing a treatment that reduces graft rejection. The present invention may also result in eliminating or reducing immunosuppressing compounds that must be administered to a patient, thus significantly reducing the patient's susceptibility to infection.

In accordance with these and other objects and advantages, an aspect of the present invention provides a method for treating an organ donor prior to harvesting organ to reduce graft rejection in a recipient and a method for reducing acute allograft graft rejection. According to these methods, an amount effective to reduce graft rejection of at least one compound selected from the group consisting of compounds having formulas I, II, III, IV, V, VI, and VII is administered to an organ donor:

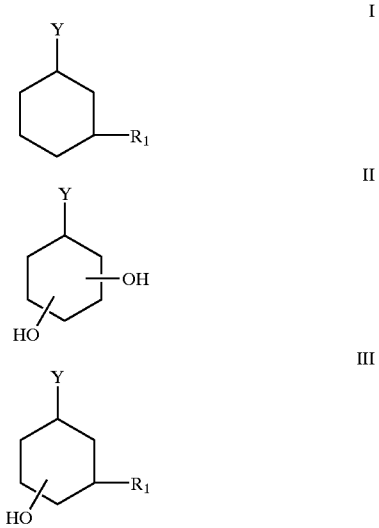

-continued

IV
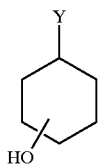

V
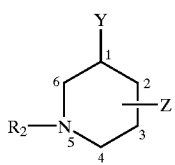

VI
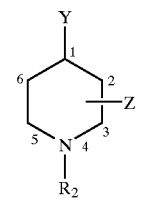

VII
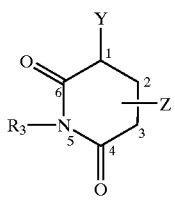

wherein
Y is

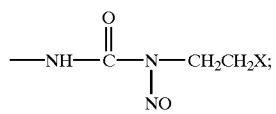

X is F or Cl;

$R_1$ is a straight or branched alkyl group having from 1 to 7 carbon atoms;

$R_2$ is a straight or branched alkyl group having from 1 to 7 carbon atoms;

$R_3$ is H or a straight or branched alkyl group having from 1 to 7 carbon atoms;

Z is H, OH, or a straight or branched alkyl group including from 1 to 7 carbon atoms; and in Formula II, the OH groups may be substituted anywhere except where Y is present and are not on the same carbon atom;

in Formula III, the OH group may be substituted anywhere except where Y is present;

in Formula IV, the OH group may be substituted anywhere except where Y is present;

in Formula V, Z may be substituted anywhere except at C-1, C-6, and C-4 if Z is OH;

in Formula VI, Z may be substituted anywhere except at C-1, C-3, and C-5 if Z is OH; and in Formula VII, Z may be at C-1, C-2, and C-3 except not on C-1 if Z is OH.

Additional aspects of the present invention provide a pharmaceutical composition that includes an amount effective to reduce graft rejection of at least one compound selected from the group consisting of compounds having the above formulas I, II, III, IV, V, VI, and VII.

Still other objects and advantages of the present invention will become readily apparent by those skilled in the art from the following detailed description, wherein it is shown and described only the preferred embodiments of the invention, simply by way of illustration of the best mode contemplated of carrying out the invention. As will be realized, the invention is capable of other and different embodiments, and its several details are capable of modifications in various obvious respects, without departing from the invention. Accordingly, the drawings and description are to be regarded as illustrative in nature and not as restrictive.

DETAILED DESCRIPTION OF THE INVENTION

As discussed above, the present invention provides methods for preventing or treating acute allograft rejection by treating an organ donor prior to harvesting of the organs from the donor. The present invention permits eliminating or reducing dosages of immunosuppressing compounds to the recipient. Eliminating or reducing dosages of immunosuppressing drugs eliminates or reduces the concomitant adverse effects associated with the drugs. In fact, it has been found that at least one compound of the present invention was more effective than Methotrexate or other known compounds when utilized as a donor pretreatment for preventing allograft rejection.

Accordingly, the present invention provides methods for treating an organ donor prior to harvesting organs to reduce graft rejection in recipient. The method includes administering to an organ donor prior to harvesting of the organ an amount effective to reduce graft rejection of at least one of the following compounds:

I
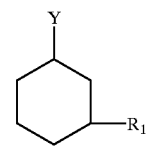

II
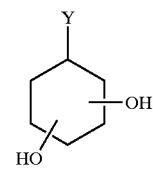

III
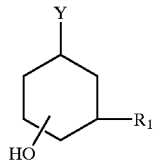

IV
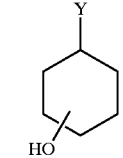

-continued

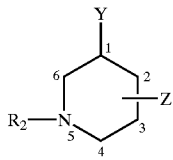

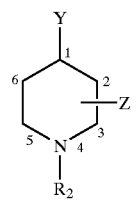

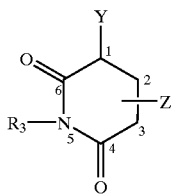

wherein
Y is

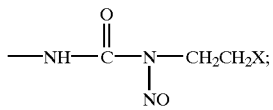

X is F or Cl;
$R_1$ is a straight or branched alkyl group having from 1 to 7 carbon atoms;
$R_2$ is a straight or branched alkyl group having from 1 to 7 carbon atoms;
$R_3$ is H or a straight or branched alkyl group having from 1 to 7 carbon atoms;
Z is H, OH, or a straight or branched alkyl group including from 1 to 7 carbon atoms; and
in Formula II, the OH groups may be substituted anywhere except where Y is present and are not on the same carbon atom;
in Formula III, the OH group may be substituted anywhere except where Y is present;
in Formula IV, the OH group may be substituted anywhere except where Y is present;
in Formula V, Z may be substituted anywhere except at C-1, C-6, and C-4 if Z is OH;
in Formula VI, Z may be substituted anywhere except at C-1, C-3, and C-5 if Z is OH; and
in Formula VII, Z may be at C-1, C-2, and C-3 except not on C-1 if Z is OH.

Administration of at least one of the above compounds may begin about 6 hours to about 24 hours prior to removal of the organ from the donor. An example of a suitable dosage is approximately the $LD_{50}$ value as determined in rats and then extrapolated to humans for the drug being administered. The dosage can be readily determined by those skilled in the art once aware of this disclosure without undue experimentation.

As a result of the treatment according to the present invention, recipients of organs from the donor's body will then not need any immunosuppressant therapy or need less immunosuppressant therapy to prevent rejection of the transplanted organ. As a result of elimination and reduction of immunosuppressant therapy, the adverse effects generally associated with the administration of large doses of immunosuppressant drugs will be reduced or eliminated. The present invention may be utilized in treating a donor for any organ transplant, including heart, kidney, pancreas, and/or liver.

Compounds of the present invention typically belong to the class of compounds known as nitrosoureas.

According to one example, the following compound:

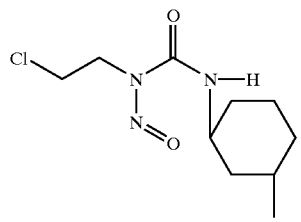

1-(2-chloroethyl)-1-nitroso-3-(3-methylcyclohexyl)urea was administered 5 mg per donor rat at a dosage of 20 mg/kg 24 hours prior to removal of heart tissue for transplantation. Administration of the compound above results in survival of 25 days, 27 days, 30 days, 32 days, and greater than 60 days.

According to this experiment, the donor rats were Fischer strain and the recipients were Long-Evans strains. These strains are mismatched at the major histocompatibility antigenic site (Ag locus). In the experiment, intra abdominal heterotopic cardiografting was performed using a modification of techniques described by Ono and Lindsey, *Improved Technique of Heart Transplantation In Rats,* Journal of Thoracic and Cardiovascular Surgery, 57: 225 (1969) and Lee et al., *Heterotopic Heart and Lung Transplantation in the Rat,* American Journal of Pathology, 59: 279 (1970), the entire contents of the disclosures of both of which are hereby incorporated by reference.

According to this experiment, a total dose of 20 milligrams per kilogram of the above compound was administered to donor rats 24 hours prior to transplantation. According to this dosage regimen, survival was prolonged from 10 to 25–60 days. Survival for 60 days indicated permanent survival, in other words, while typically surviving 10 days, the rats lived for 25–60 days, with the rats living to 60 days having a permanent survival. The rats surviving for 60 days were sacrificed after two years and microscopic evaluation revealed normal hearts.

When 20 milligrams per kilogram of the above compound was combined with 100 milligrams per kilogram of methotrexate in treating donors, an increase in median survival (considering dying rats only) over administration of the compound alone occurred.

Moreover, when the recipients were also treated with a single small dose of Cyclosporine A, this produced an increase in survival.

Specific compounds according to the present invention that have shown activity in reducing acute allograft rejection include:

The latter compound demonstrated the following degree of activity:

| Dose/rat | Days of Survival |
|---|---|
| 0.5 mg | 67 |
| 2.5 mg | 18 |
| 5.0 mg | 8, 12, 22, 13, 28 |

The foregoing description of the invention illustrates and describes the present invention. Additionally, the disclosure shows and describes only the preferred embodiments of the invention, but as aforementioned, it is to be understood that the invention is capable of use in various other combinations, modifications, and environments and is capable of changes or modifications within the scope of the inventive concept as expressed herein, commensurate with the above teachings, and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

We claim:

1. A method for treating an organ donor prior to harvesting an organ to reduce graft rejection in a recipient, the method comprising the steps of:

administering to the organ donor an amount effective to reduce graft rejection of at least one compound selected from the group consisting of compounds having formulas I, II, III, IV, V, VI, and VII:

wherein
Y is

X is F or Cl;
$R_1$ is a straight or branched alkyl group having from 1 to 7 carbon atoms;
$R_2$ is a straight or branched alkyl group having from 1 to 7 carbon atoms;

R₃ is H or a straight or branched alkyl group having from 1 to 7 carbon atoms;

Z is H, OH, or a straight or branched alkyl group including from 1 to 7 carbon atoms; and in Formula II, the OH groups may be substituted anywhere except where Y is present and are not on the same carbon atom;

in Formula III, the OH group may be substituted anywhere except where Y is present;

in Formula IV, the OH group may be substituted anywhere except where Y is present;

in Formula V, Z may be substituted anywhere except at C-1, C-6, and C-4 if Z is OH;

in Formula VI, Z may be substituted anywhere except at C-1, C-3, and C-5 if Z is OH; and in Formula VII, Z may be at C-1, C-2, and C-3 except not on C-1 if Z is OH.

2. The method according to claim 1, wherein the compound administered to the organ donor is:

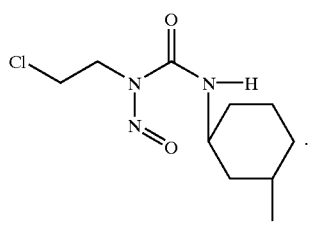

3. The method according to claim 1, wherein the compound administered to the organ donor is:

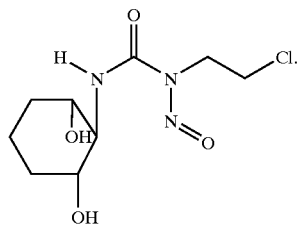

4. The method according to claim 1, wherein the compound administered to the organ donor is:

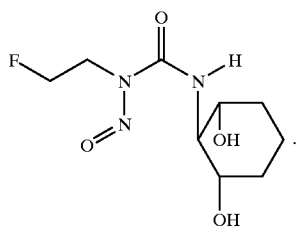

5. The method according to claim 1, wherein the compound administered to the organ donor comprises:

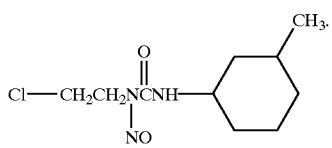

6. The method according to claim 1, wherein the compound administered to the organ donor is:

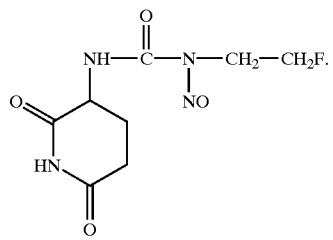

7. A method of reducing acute allograft graft rejection, the method comprising the step of:

administering to an organ donor an amount effective to reduce graft rejection of at least one compound selected from the group consisting of compounds having formulas I, II, III, IV, V, VI, and VII:

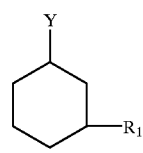

I

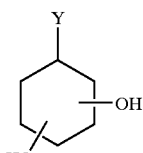

II

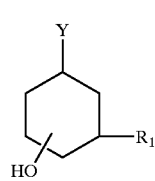

III

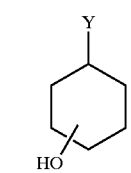

IV

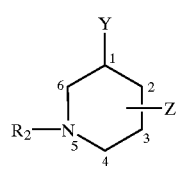

V

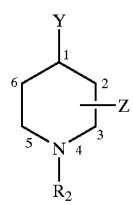

VI

-continued

VII

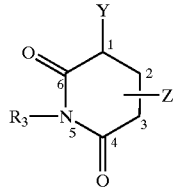

wherein
Y is

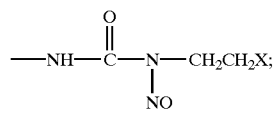

X is F or Cl;
R₁ is a straight or branched alkyl group having from 1 to 7 carbon atoms;
R₂ is a straight or branched alkyl group having from 1 to 7 carbon atoms;
R₃ is H or a straight or branched alkyl group having from 1 to 7 carbon atoms;
Z is H, OH, or a straight or branched alkyl group including from 1 to 7 carbon atoms; and
in Formula II, the OH groups may be substituted anywhere except where Y is present and are not on the same carbon atom;
in Formula III, the OH group may be substituted anywhere except where Y is present;
in Formula IV, the OH group may be substituted anywhere except where Y is present;
in Formula V, Z may be substituted anywhere except at C-1, C-6, and C-4 if Z is OH;
in Formula VI, Z may be substituted anywhere except at C-1, C-3, and C-5 if Z is OH; and
in Formula VII, Z may be at C-1, C-2, and C-3 except not on C-1 if Z is OH.

8. The method according to claim 7, wherein the compound administered to the organ donor is:

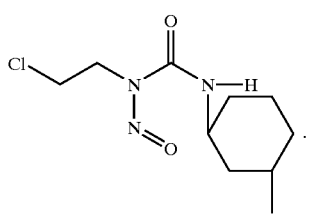

9. The method according to claim 7, wherein the compound administered to the organ donor is:

10. The method according to claim 7, wherein the compound administered to the organ donor is:

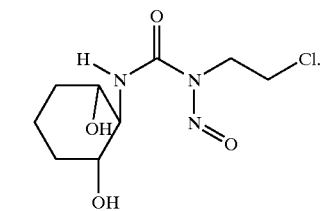

11. The method according to claim 7, wherein the compound administered to the organ donor comprises:

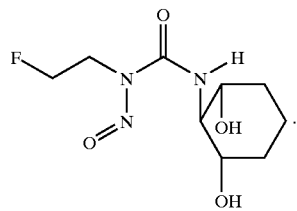

12. The method according to claim 7, wherein the compound administered to the organ donor is:

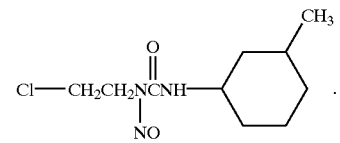

13. The method according to claim 7, further comprising the step of:
further administering to the recipient at least one additional immunosuppressive compound.

14. The method according to claim 13, wherein the immunosuppressive compound comprises Cyclosporine A.

* * * * *